United States Patent
Deshpande et al.

(12) 
(10) Patent No.: US 6,610,845 B1
(45) Date of Patent: Aug. 26, 2003

(54) THIOESTER DERIVATIVES OF THIAZOLYL ACETIC ACID AND THEIR USE IN THE PREPARATION OF CEPHALOSPORIN COMPOUNDS

(75) Inventors: Pandurang Balwant Deshpande, Tamilnadu (IN); Pramod Narayan Deshpande, Tamilnadu (IN); Shanmugam Srinivasan, Tamilnadu (IN); Parven Kumar Luthra, Tamilnadu (IN); Gautam Kumar Das, Chennai (IN)

(73) Assignee: Orchid Chemicals & Pharmaceuticals Limited, India, Tamil Nadu (IN)

( * ) Notice: Subject to any disclaimer, the term of this patent is extended or adjusted under 35 U.S.C. 154(b) by 0 days.

(21) Appl. No.: 10/035,177

(22) Filed: Jan. 4, 2002

(51) Int. Cl.$^7$ ............... C07D 501/36; C07D 501/34; C07D 501/56; C07D 501/22; C07D 417/12
(52) U.S. Cl. ............ 540/215; 540/225; 540/227; 540/228; 544/182
(58) Field of Search ............... 544/182; 540/225, 540/227, 228, 215

(56) References Cited

U.S. PATENT DOCUMENTS

| | | | |
|---|---|---|---|
| 4,385,181 A | * 5/1983 | Farge et al. | 544/182 |
| 4,548,748 A | 10/1985 | Van Rheenen | |
| 4,576,749 A | 3/1986 | Zahler et al. | |
| 4,767,852 A | 8/1988 | Ascher | |
| 5,026,843 A | 6/1991 | Riccardo et al. | |
| 5,037,988 A | 8/1991 | Meseguer et al. | |
| 5,856,502 A | 1/1999 | Datta et al. | |
| 5,869,649 A | 2/1999 | Khanna et al. | |

OTHER PUBLICATIONS

Donald G. Walker, "New Cephalosporin Acylating Agents Derived from Syn–2–(2–Aminothiazol–4–YL)–2–Methoxyiminoacetic Acid. Application to the Synthesis of Cefepime Sulfate." vol. 31, No. 45, PP 6481–6484, 1990, Syracuse, New York.
Chemical Abstracts, vol. 111, pp. 220–221, 1989.

* cited by examiner

Primary Examiner—Mark L. Berch
(74) Attorney, Agent, or Firm—Burns, Doane, Swecker & Mathis, L.L.P.

(57) ABSTRACT

The present invention provides new thioester derivatives of thiazolyl acetic acid of the general formula (I),

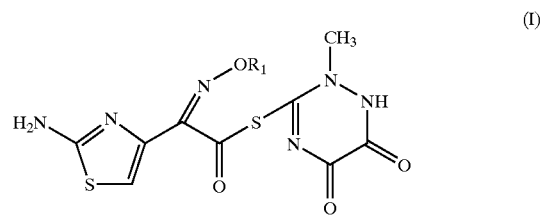

(I)

wherein, $R_1$ represents H, trityl, $CH_3$, $CR_aR_bCOOR_2$ ($R_a$ and $R_b$ independently of one another represents hydrogen or methyl and $R_2$ represents H or $C_1$–$C_4$ alkyl).
also, the invention provides a method by which the said thioester derivatives can be prepared by reacting thiazolyl acetic acid of the general formula (IV) with 1,2,5,6 tetrahdro-2-methyl-5,6 dioxo-1,2,4-triazin-3-thiol of the formula (VI) in a

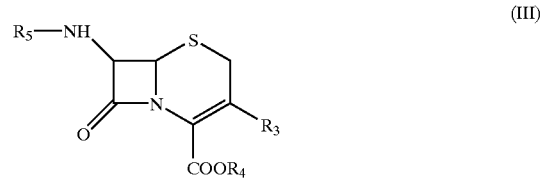

(III)

solvent, in presence of an organic base and with the help of Vilsmeier reagent of the formula (V). The so obtained thioester derivatives are reacted with 7-amino-cephem carboxylic acids of the general formula (III) to produce cephalosporin antibiotic compounds having the general formula (II).

11 Claims, No Drawings

THIOESTER DERIVATIVES OF THIAZOLYL ACETIC ACID AND THEIR USE IN THE PREPARATION OF CEPHALOSPORIN COMPOUNDS

FIELD OF INVENTION

The present invention relates to novel thioester derivatives of thiazolyl acetic acid of the general formula (I), useful as an intermediate for the preparation of cephalosporin antibiotics having the general formula (II). In addition, the present invention also relates to a process for preparation of cephalosporin antibiotics using the said thioester derivatives.

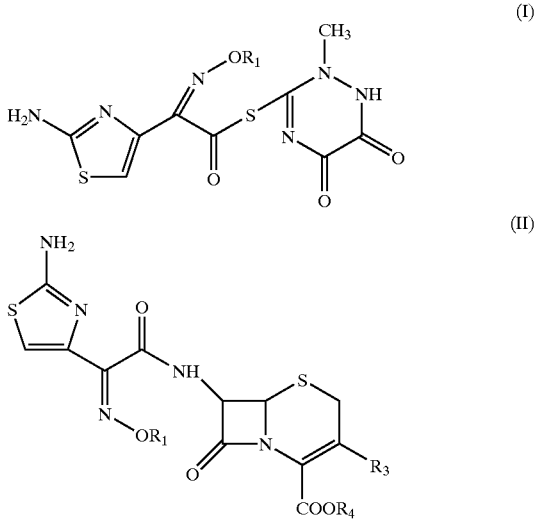

Wherein, $R_1$ represents H, trityl, $CH_3$, $CR_aR_bCOOR_2$ ($R_a$ and $R_b$ independently of one another represent hydrogen or methyl and $R_2$ represents H or $C_1$–$C_4$ alkyl).

BACKGROUND OF THE INVENTION

Use of acid chlorides, anhydrides, esters, amide etc. are reported in the chemical literature for activation of carboxylic acid of formula (IV). Activation in the form

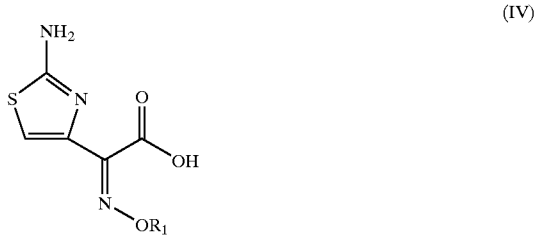

of acid chloride required protection and deprotection of $NH_2$ group.

Activation of acid (IV) is reported by $SO_2Cl_2$/DMF in U.S. Pat. No. 5,856,502 and $SOCl_2$/DMF in U.S. Pat. No. 5,037,988. These processes suffer the limitation of using harmful and pungent smelling chemicals like $SOCl_2$, $SO_2Cl_2$ along with solvents like benzene, toluene, etc. and involving stringent conditions for carrying out the reactions at commercial scale.

In U.S. Pat. Nos. 4,576,749 and 4,548,748, the acid of formula (IV) has also been activated by reacting with 1-hydroxybenzotriazole (HOBT) or 2-mercaptobenzothiazole (MBT) in the presence of dicyclohexylcarbodiimide (DCC) to produce reactive ester of the acid (IV) which is then reacted with cephem moiety to prepare cephalosporin antibiotics, but the processes are time consuming accompanied with low yields, hence, not suitable.

U.S. Pat. No. 4,767,852 discloses a process for production of cephems by acylating 7-amino-3-cephem-4-carboxylic acid with 2-mercaptobenzothiazolyl-(Z)-2-(2-aminothiazol-4-yl)-2-methoxyiminoacetate (MAEM). Similarly, U.S. Pat. No. 5,026,843 (1991) disclosed a process for preparing ceftriaxone disodium hemiheptahydrate by acylation of 7-amino-3-[(2,5-dihydro-6-hydroxy-2-methyl-5-oxo-1,2,4-triazin-3yl) thiomethyl]-3-cephem-4-carboxylic acid (7-ACT) by using MAEM as acylating agents in good yield and quality. Thus MAEM has become the standard acylating agent for the preparation of cephalosporins antibiotics having an oximino group and a 2-aminothiazolyl group in 7-position of cephem compounds.

However, the synthesis of MAEM from acid (III) and 2,2'-dithio-bis-benzothiazole involves use of costly condensing agent triphenylphosphine (TPP). Moreover, during condensation of MAEM with 7-amino-3-cephem-4-carboxylic acid compound (III), a toxic compound 2-mercaptobenzothiazole (MBT) is also produced as a byproduct [Chemical Abstracts, 111, p.19243 (1989)], which is difficult to remove.

Thus, it is evident that the procedures described in the prior art for the preparation of these cephalosporin antibiotics are complex, involving protection, deprotection and also associated with generation of toxic byproduct. Hence, there is a need to develop new acylating agents which are capable of transferring the 2-aminothiazolyl moiety to cephem compounds of formula (III) in good yield, without producing this toxic byproduct. On the similar lines, a new thioester was reported by D. G. Walker, Tet. Lett. 1990, 31,6481 to acylate the cephem moiety to get cefepime sulfate but yields obtained by using this thioester were in the range of 54–73% which cannot be considered as good yield to operate a process at commercial scale. The same thioester is exploited in U.S. Pat. No. 5,869,649 for making three more important cephalosporin antibiotics.

OBJECTIVES OF THE INVENTION

In the co pending application U.S. application Ser. No. 09/754,302, U.S. Pat. No. 6,388,070 the Applicant has disclosed another novel thioester derivative of thiazole acetic acid & its use in the synthesis of various cepalosporin antibiotics. In continuation of search for more such derivatives, the Applicant observed that the title compound (I) works equally well and also has the similar advantages as described in the aforementioned US application.

The primary objective of this invention is to prepare a new thioester derivative of thiazolyl acetic acid of the formula (I), which would be better than the earlier reactive derivatives and also suitable for being used in the manufacture of cephalosporin antibiotics.

Another objective of the present invention is to provide a process for the synthesis of thioester derivative of formula (I) from thiazolyl acetic acid of the formula (IV) and 1,2,5,6 tetrahydro-2-methyl-5,6-dioxo-1,2,4-triazin-3-thiol (VI).

Yet another objective of the present invention is to provide a process for the preparation of cephalosporin antibiotics of the general formula (II) at low temperature, which will be simple and cost effective.

Still another objective of the present invention is to produce cephalosporin antibiotics that are high purity and free from toxic byproducts.

One more objective of the present invention is to provide a process for the preparation of cephalosporin antibiotics of the general formula (II) from the said novel thioester derivatives.

SUMMARY OF THE INVENTION

The present invention provides a new thioester derivatives of thiazolyl acetic acid of formula (I) and also provides a method by which the said thioester derivatives can be prepared by reacting thiazolyl acetic acid of the general formula (IV) with the commercially available 1,2,5,6 tetrahydro-2-methyl-5,6 dioxo-1,2,4-triazin-3-thiol (VI) using Vilsmeier reagent (V) as a condensing agent. (Ber. 60B, 119 (1927). The thioester derivatives thus obtained are reacted with 7-amino-cephem carboxylic acids of the general formula (III) to produce cephalosporin antibiotic compounds of the general formula (II), as described above. The cephalosporin antibiotics obtained are of high purity (95–99%). The method is workable at commercial scale without necessitating for the protection of the amino group of the acylating agents, and avoiding the generation of the toxic byproduct 2-mercaptobenzothiazole.

DETAILED DESCRTIPTION OF THE INVENTION

1. The present invention provides a process for the preparation of a new thioester of the formula (I), as mentioned earlier. The said process comprises condensation of thiazolylacetic acid represented by formula (IV)

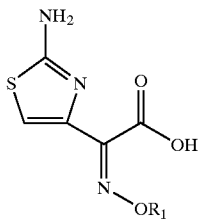

(IV)

wherein, $R_1$ represents H, trityl, $CH_3$, $CR_aR_bCOOR_2$ ($R_a$ and $R_b$ independently of one another represents hydrogen or methyl and $R_2$ represents H or $C_1$–$C_4$ alkyl).

with 1,2,5,6 tetrahdro-2-methyl-5,6 dioxo-1,2,4-triazin-3-thiol of formula (VI)

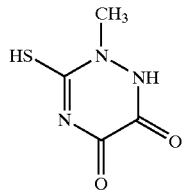

(VI)

In presence of Vilsmeier reagent of the formula (V) in an organic solvent.

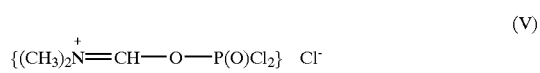

(V)

at temperature being maintained in the range –10° C. to +30° C.

The thioester of general Formula (I) thus obtained is reacted with 7-amino cephem carboxylic acids of the general formula (III) in organic solvent in presence of organic base to obtain cephalosporin antibiotics of the general formula (II).

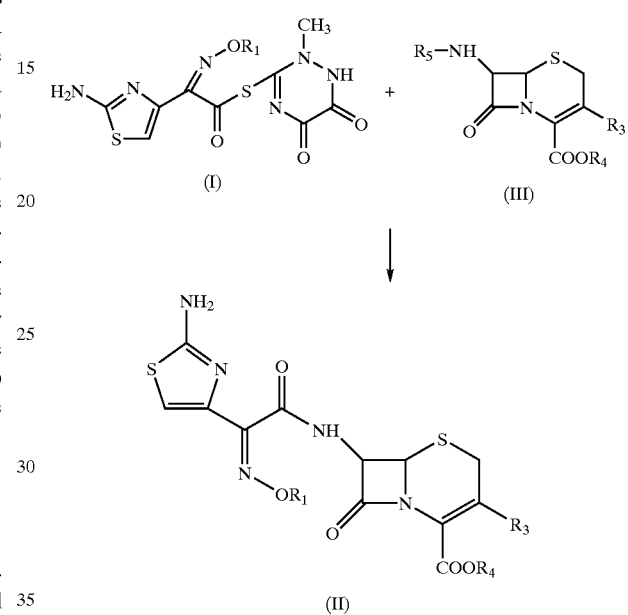

wherein, in formula (I), $R_1$ represents H, trityl, $CH_3$, $CR_aR_bCOOR_2$ ($R_a$ and $R_b$ independently of one another represents hydrogen or methyl and $R_2$ represents H or $C_1$–$C_4$ alkyl).

In formula (III) $R_3$ represents $CH_3$, $-CH=CH_2$, $CH_2OCH_3$, $CH_2OCOCH_3$,

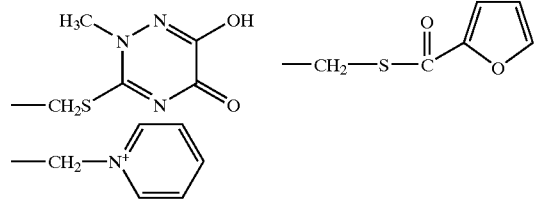

$R_4$ is hydrogen, salt, carboxylic protecting group or an inner salt.

$R_5$ is hydrogen or trialkylsilyl.

wherein formula (II), $R_1$, $R_3$ and $R_4$ are as defined above.

Another embodiment of the present invention provides a method by which cephalosporin antibiotics are obtained in high purity and excellent yield without the necessity for protecting the amino group of the acylating agents and avoiding the production of toxic byproduct namely 2-mercaptobenzothiazole(MBT).

In one another embodiment of the present invention, the substituent $R_3$ in cephem compound (II) and (III) represents methyl, acetyloxymethyl, methoxymethyl, vinyl, pyridylmethyl, propenyl, 2,5-dihydro-6-hydroxy-2-methyl- 5-oxo-1,2,4-triazine-3-thiol, furanyl-2-carbonylthiol. In general, $R_3$ represents —$CH_2$—X wherein X is a residue of any organic or inorganic nucleophilic compound, e.g., halogen, hydroxy, cyano, mercapto, azido, amino, etc. Furthermore, X may preferably represent residue of any 5 or 6 membered heterocyclic thiol.

In yet another embodiment of the present invention, the substituent $R_4$ represents hydrogen, salt, a standard carboxylic protecting group, or a inner salt. Especially it is termed as carboxylate ion when $R_3$ is pyridylmethyl, which ultimately explains the neutrality of the molecules.

Another embodiment of the invention provides the use of Vilsmeier reagent of formula (V) as condensing agent.

Still another embodiment of the invention provides acylation of (III) (when $R_5$ is H) is performed in presence of a water miscible solvent like tetrahydrofuran (THF), acetonitrile, acetone, dioxane, N,N-dimethylformamide etc. but the preferable solvents are THF and acetonitrile.

In an embodiment of the present invention, acylation of (III) (when $R_5$ is trimethylsilyl) is carried out in aprotic organic solvents like halogenated hydrocarbons, toluene, acetonitrile, alkyl ethers etc., but preferable solvent is acetonitrile and dichloromethane. More suitable silylating agents used for the reaction are hexamethyldisalazane, bis(trimethyl)silylacetamide and trimethylsilyl chloride or a mixture thereof.

In yet another embodiment of the present invention, the organic base may be selected from triethylamine, diethylamine, tributylamine, N-alkylpipridine, N-alkylanilines, 1,8-diazabicyclo[5.4.2]undec-7-ene, 1,5-diazabicyclo[4.3.0]non-5-ene, N-methylmorpholine, 1,4-diazabicyclo[2.2.2]octane, 4-dimethylamino pyridine and mixtures thereof.

The conceptual utility of this new thioesters of 1,2,5,6 tetrahdro-2-methyl-5,6 dioxo-1,2,4-triazin-3-thiol of the general formula (VI) is also tried in various coupling reactions of carboxylic acids and amines. Most of amide formation reactions have shown good results. L-alanine, 5-methylisoxazole-4-carboxylic acid, 2-thienylacetic acid, etc. are some of the compounds, which have been activated by above mentioned thiol of formula (VI). Some of the results are summarized in the following table.

| S. No. | Acids | Amines | % by HPLC |
|---|---|---|---|
| 1. | 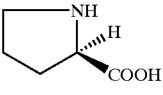 | 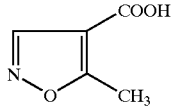 | 63–78% |
| 2. |  | 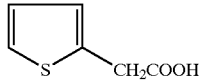 | 79–91% |
| 3. | | 7-Amino cephalosporanic acid | 84–87% |

Many other beneficial results are obtained by applying disclosed invention in a different manner or by modifying the invention with the scope of disclosure. However, since the major characteristic feature of the present invention resides in the use of novel reactive thioester derivatives of thiazolyl acetic acid of the general formula (I) in preparing the cephalosporin antibiotics, the technical scope of the present invention should not be limited to the following examples.

The invention is illustrated with the following examples, which should not be construed as limiting the scope of the invention.

EXAMPLE-I

Synthesis of 1,2,5,6 Tetrahydro-2-methyl-3-thio-5,6 Dioxo-1,2,4-triazine-(Z)-2-(2-aminothiazol-4-yl)-2-methoxyimino Acetate (I)

To the cold Dimethylformamide (DMF), (50 g), phosphorousoxychloride ($POCl_3$) (84 g) was added slowly in 30 min and stirred at 0–10° C. Acetonitrile 1.0 lit was added and reaction mass cooled further to −20 to −45° C. and (Z)-(2-aminothiazol-4-yl)methoxyimino acetic acid (100 g) was added and stirred for 30 min. 1,2,5,6 tetrahydro-2-methyl-5,6 dioxo-1,2,4-triazine-3-thiol (96 g) followed by pyridine (198 g) was added . The reaction mixture was stirred for 30 min. After the reaction was complete, distilled water 1800 ml was added to the reaction solution and the mixture was stirred for 10 min. The product was filtered, washed with water (1.0 lit) and acetone (1.0 lit) Dried to obtain 146 g (yield 86%) of the title compound as light yellow solid.

Melting point: 187° C.; $^1$HNMR (DMSO-$d_6$): δ 3.78 (3H,s,N—$CH_3$), 3.96 (3H,s,N—$OCH_3$), 7.4 (1H,s, thiazole ring proton), 7.25(2H,bs,$NH_2$), 13.9 (1H, s,OH); $^{13}$CNMR (DMSO$d_6$):δ45.6,64.0,112.3,141.0,144.6,146.5,149.3, 159.5,169.8,174.4. .Mass spectra: $M^+$ peak=343.

EXAMPLE-II

7-[[(Z)-2-(2-Aminothiazol-4-yl)2-methoxyimino] acetamido]-3-[[(2,5-dihydro-6-hydroxy-2-methyl-5-oxo-1,2,4-triazin-3-yl)thio]methyl]-3-cephem-4-carboxylicacid Disodium Hemiheptahydrate (Ceftriaxone Sodium)

7-Amino-3-[(2,5-dihydro-6-hydroxy-2-methyl-5-oxo-1, 2,4-triazin-3yl) thiomethyl]3-cephem-4-carboxylic acid (60 g) and 1,2,5,6 tetrahydro-2-methyl-3-thio-5,6dioxo-1,2,4-triazine-(Z)-2-(2-aminothiazol-4-yl)-2-methoxyimino acetate (I) (92 g) were suspended in a mixture of THF (450 ml) and $H_2O$ (250 ml) maintained at 0°–5° C. under stirring. Triethylamine (68.7 ml) was added in 2–3 hours at 5° C. maintaining the pH 7.5–8.5. The reaction progress was monitored by HPLC. After the reaction was complete, the mixture was extracted with ethylacetate (400 ml). Sodium-2-ethylhexanoate (55 g) was added to the aqueous solution and acetone (1.0 lit) was added in 1 hour at 10–15° C. to complete the crystallization. The product was filtered under $N_2$ atmosphere and wet cake was dissolved in mixture of water and acetone (1:2 by volume), and cooled to −10 to −15° C. Coloured impurities were separated. The solution was decanted and diluted with acetone (2500 ml) at 18–20° C. Precipitated solid was filtered under $N_2$ and washed with acetone (200 ml). Dried under vacuum at 40–45° C. to get pure Ceftriaxone sodium, 95 g. which was once again crystallized in sterile area in water—acetone (1:4 by volume) mixture to get sterile product. (85 g) (yield=80%) HPLC (purity):98–99.5%.

Example-III

7-[[(Z)-2-(2-Aminothiazol-4-yl)2-methoxyimino] acetamido]-3-[[(2,5-dihydro-6-hydroxy-2-methyl-5-oxo-1,2,4-triazin-3-yl)thio]methyl]-3-cephem4-carboxylicacid Disodium Hemiheptahydrate (Ceftriaxone Sodium)

7-Amino-3-[[(2,5-dihydro-6-hydroxy-2-methyl-5-oxo-1, 2,4-triazin-3yl)thio]methyl]3-cephem-4-carboxylic acid (20.0 g) was suspended in dichloromethane (200 ml). To this was added hexamethyldisilazane (17.0 g) and trimethylsilyl chloride (3.0 g). The suspension was refluxed for 2–3 hours to get clear solution. Cooled to 0° C. and triethylamine (13.6 g) was added slowly. At the same temperature, 1,2,5,6 tetrahydro-2-methyl-3-thio-5,6 dioxo-1,2,4-triazine-(Z)-2-(2-aminothiazol-4-yl)-2-methoxyimino acetate (I) (20 g) was added. The reaction mixture was monitored by HPLC. After completion of reaction, 200 ml water was added and pH was adjusted to 7.0. The aqueous layer was separated, charcoalized and treated with sodium-2-ethylhexanoate (18.5 g) in acetone, reaction was proceeded by same method as mentioned in Ex-II to get final sterile ceftriaxone sodium (28.0 g)

Example-IV

3-Acetyloxymethyl-7-[(Z)-(2-aminothiazolyl-4-yl)-2-(Methoxyimino) Acetamido]-3-cephem-4-carboxylic Acid (Cefotaxime Sodium)

A mixture of THF (200 ml) and water (150 ml) was stirred under inert atmosphere. At 0°–1° C., 7-aminocephalosporanic acid (25.0 g) and 1,2,5,6 tetrahydro-2-methyl-3-thio-5,6 dioxo-1,2,4-triazine-(Z)-2-(2-aminothiazol-4-yl)-2-methoxyimino acetate (I) (39.8 g) were added. Triethylamine (10.4 g) was slowly added to reaction by maintaining pH 7.5 to 8.5. The reaction was followed by HPLC. After 4–5 hrs., the reaction mixture was extracted by ethylacetate. The aqueous layer is subjected for charcoal (0.125 g) treatment. Ethylacetate was added to the filtrate and the solution was acidified with dil. HCl at 10° C. to pH 3.0. The solid separated was filtered, washed with water and ethylacetate and then dried under vacuum at 40–45° C. to get Cefotaxime, 40.9 g (yield 98%). The Cefotaxime acid was dissolved in water at pH 6.5 using sodium carbonate. The solution was filterd through 0.2 micron under aseptic conditions & the product is crystallized by addition of acetone. Yield 38 g HPLC (purity)=98–99%.

Example-V

7-[[(Z)-2-(Aminothiazol-4-yl)-2-methoxyimino] acetamino]-3-methoxymethyl-3-cephem-4-carboxylic Acid[Cefpodoxime Acid]

7-Amino-3-methoxymethyl-3-cephem-4-carboxylic acid (24.2 g) and 1,2,5,6 tetrahydro-2-methyl-3-thio-5,6 dioxo-1,2,4-triazine-(Z)-2-(2-aminothiazol-4-yl)-2-methoxyimino acetate (I). (35 g) were suspended in 400 ml of THF and water mixture (1:1). At 10° C. Triethylamine (TEA) 9.0 gms added to maintain pH 7–8. The reaction was monitored and proceeded as described in example II. To the separated aq. layer, pH was adjusted to 2.7 using 16–18% sulphuric acid. Solid was cooled to 10° C., filtered and washed with water (3×50ml) and finally with acetone (20 ml) to obtain the Cefpodoxime acid, 37.5 g (yield 88%).

HPLC (purity):98.0%.

Example-VI

Sodium -7-[[(Z)-2-(Aminothiazol-4-yl)-2-methoxyimino]acetamido]-3-(2-furanylcarbonyl) Thiomethyl]-3-cephem4-carboxylate (Sterile Buffered Ceftiofur Sodium)

7-Amino-3-[(2-furanylcarboxyl)thiomethyl]-3-cephem-4-carboxylic acid (30.0 g, 88.2 mmol) and 2-mercapto-5-phenyl-1,3,4-oxadiazolyl-(Z)-2-(2-aminothiazol-4-yl)-2-methoxyimino acetate (47.7 g, 132.0 mmol) are added to a mixture of dichloromethane (400 ml) and methanol (15 ml) at temperature 0–5° C. Triethylamine(25.0 ml) is added to the reaction mixture in 50–60 min. After completion of reaction, the reaction mixture is extracted with water (400 ml). The aqueous layer is separated and treated with charcoal (0.500 g). Tetrahydrofuran (400 ml) and 100 g of sodium chloride is added to this solution followed by addition of (9.2 ml) of hydrochloric acid (35%). The mixture is srirred for 10 min and layers are separated. Tetrahydrofuran layer is treated with charcoal and added to another 75 ml solution tetrahydrofuran containing 13.5 g of sodium-2-ethylhexanoate under stirring. To this solution slowly tetrahydrofuran(550 ml) is added at a temperature of 20° C., white to creamish solid precipitated out in the solution, which is cooled to 0–5° C. for 2.0 h. Ceftiofur sodium thus prepared is filtered under inert atmosphere, washed with acetone and dried under vacuum to get 36–38 g of ceftiofur sodium with HPLC (purity) of 98.0%. The ceftiofur sodium thus prepared is dissolved in water (350 ml). The pH of the solution is adjusted to 7.5 by adding sodium bicarbonate. Potassium dihydrogen phosphate(1.0–1.5 g) is added ,the solution is filtered through a 0.2 micron filter under sterile condition and subjected to lyophilisation to obtain sterile buffered ceftiofur sodium (37–38 g).

We claim:
1. A process for preparing a compound of formula (II)

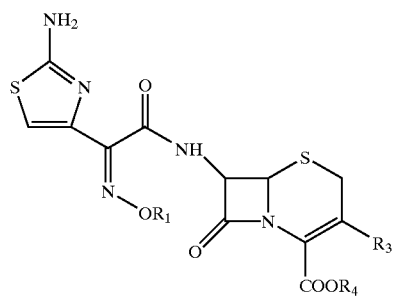

(II)

wherein, $R_1$ represents H, trityl, $CH_3$, $CR_aR_bCOOR_2$ ($R_a$ and $R_b$ independently of one another represents hydrogen or methyl and $R_2$ represents H or $C_{1-4}$ alkyl);

$R_3$ is $CH_3$, —CH=$CH_2$, $CH_2OCH_3$, $CH_2OCOCH_3$,

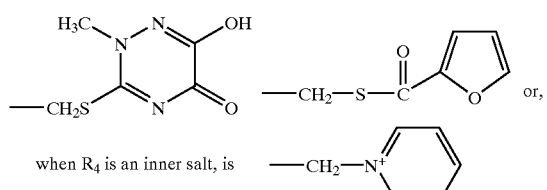

or, when $R_4$ is an inner salt, is $R_4$ is H or a salt or a carboxylic protecting group or a inner salt when $R_3$ is

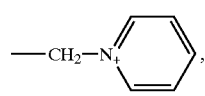, comprising acylating a compound of formula (III)

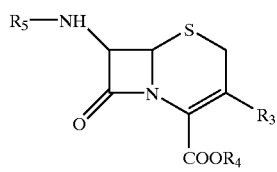
(III)

wherein, $R_5$ is H or trimethylsilyl; $R_3$ and $R_4$ are defined as above with a compound of formula I

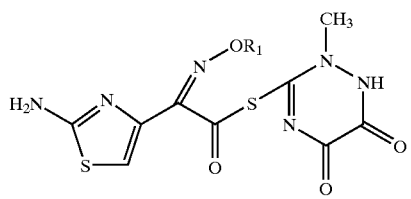
(I)

wherein, $R_1$ is as defined above, in the presence of an organic solvent and a base at a temperature in the range of $-10°$ C. to $+30°$ C.

2. The process of claim 1, wherein $R_4$ is hydrogen or alkali metal salt or an inner salt.

3. The process of claim 1, wherein said compound of formula II is a syn isomer.

4. The process of claim 1, wherein $R_5$ is H, the acylation is carried out in the presence of water and an organic solvent selected from the group consisting of tetrahydrofuran, N,N-dimethylformamide, dioxane, acetone, acetonitrile and mixtures thereof.

5. The process of claim 1, wherein $R_5$ is trimethylsilyl, the acylation is achieved by doing the reaction in aprotic organic solvent selected from the group consisting of halogenated hydrocarbon, toluene, alkyl ether, acetonitrile and mixtures thereof.

6. The process of claim 1, wherein said acylation is performed in the presence of an organic base selected from the group consisting of triethylamine, N-methylmorpholine, 1,5-diazabicyclo[4.3.0] non-5-ene, 1,4-diazabicyclo[2.2.2] octane, 4-dimethylaminopyridine, diethylamine, tributylamine, pyridine, N-alkylpyridine, N-alkylanilines, 1,8-diazabicyclo[5.4.2]undec-7-ene and mixtures thereof.

7. The process of claim 1, wherein when $R_1$ is methyl, $R_3$ is methyl, $R_3$ is (2,5-dihydro-6-hydroxy-2-methyl-5-oxo-1,2,4-triazin-3-yl)thiomethyl, purification of this compound is achieved by dissolving the crude product in mixture of water and water miscible organic solvent selected from the group consisting of acetone, isopropylalcohol, dioxane and mixtures thereof.

8. The process of claim 1, wherein when $R_1$ is methyl, $R_3$ is (2,5-dihydro-6-hydroxy-2-methyl-5-oxo-1,2,4-triazin-3-yl)thiomethyl, the colour impurities are separated at $-10°$ C. to $0°$ C. and precipitation is effected by water miscible organic solvent selected from the group consisting of acetone, isopropylalcohol, dioxane and mixtures thereof.

9. A process for preparing thiazol-4-yl acetic acid derivative represented by formula (I):

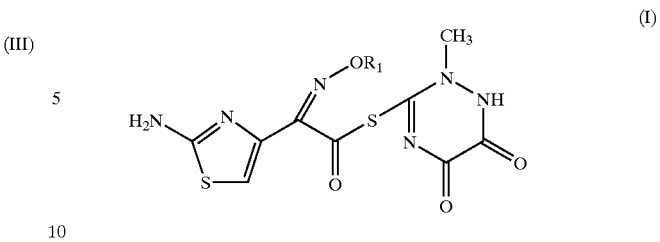
(I)

wherein $R_1$ represents H, trityl, $CH_3$, $CR_aR_bCOOR_2$ ($R_a$ and $R_b$ independently of one another represents hydrogen or methyl and $R_2$ represents H or $C_1$–$C_4$ alkyl), the process comprising condensation of thiazol-4-yl acetic acid represented by formula (IV)

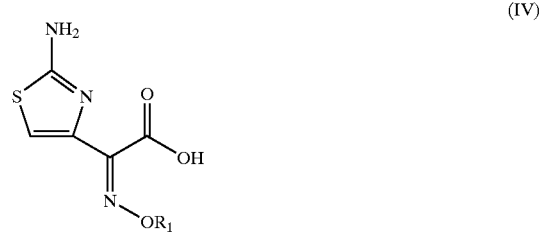
(IV)

with 1,2,5,6-tetrahydro-2-methyl-5,6-dioxo-1,2,4-triazin-3-thiol of formula (VI)

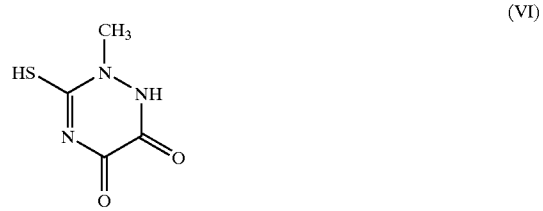
(VI)

in the presence of a Vilsmeier reagent of formula (V):

$$((CH_3)_2N^+=CH—O—P(O)Cl_2)Cl^-  \quad (V)$$

in an organic solvent and a base at a temperature being maintained in the range $-10°$ C. to $+30°$ C.

10. The process of claim 9, wherein the organic solvent is selected from the group consisting of dichloromethane, tetrahydrofuran, dioxane, N,N-dimethylformamide, acetone, acetonitrile and mixtures thereof.

11. The process of claim 9, wherein the organic base is selected from the group consisting of triethylamine, N-methylmorpholine, 1,5-diazabicyclo[4.3.0]non-5-ene, 1,4-diazabicyclo[2.2.2]octane, 4-dimethylamino pyridine, diethylamine, tributylamine, pyridine, N-alkyl-piperdine, N-alkylanilines, 1,8-diazabicyclo[5.4.2]undec-7-ene or mixtures.

* * * * *